United States Patent [19]

O'Connor et al.

[11] Patent Number: 4,485,822
[45] Date of Patent: Dec. 4, 1984

[54] MULTI-PHASE INTERFACING SYSTEM AND METHOD

[75] Inventors: George L. O'Connor, Nesconset; Ralph E. Oswald, Lindenhurst, both of N.Y.; Marc A. Heppding, Crofton, Md.

[73] Assignee: G & R Instrument Company, Inc., Lindenhurst, N.Y.

[21] Appl. No.: 461,878

[22] Filed: Jan. 28, 1983

[51] Int. Cl.³ ............................................. A61B 5/08
[52] U.S. Cl. .................................. 128/719; 128/730; 128/207.17; 128/207.18; 128/DIG. 26; 73/863.23; 422/84
[58] Field of Search ............... 128/716, 718, 719, 730, 128/200.26, 207.14, 207.17, 207.18, DIG. 26; 422/84; 73/863.23

[56] References Cited

U.S. PATENT DOCUMENTS

| | | | |
|---|---|---|---|
| 3,422,817 | 1/1969 | Mishkin et al. | 128/207.14 |
| 3,799,149 | 3/1974 | Rummel et al. | 128/718 |
| 4,178,919 | 12/1979 | Hall | 128/719 |
| 4,282,871 | 8/1981 | Chodorow | 128/DIG. 26 |
| 4,326,515 | 4/1982 | Shaffer et al. | 128/207.17 |
| 4,331,143 | 5/1982 | Foster | 128/207.17 |
| 4,378,012 | 3/1983 | Brown | 128/207.17 |
| 4,456,014 | 6/1984 | Buck et al. | 128/719 |

Primary Examiner—Lee S. Cohen
Attorney, Agent, or Firm—Leonard Belkin

[57] ABSTRACT

A system and method for interfacing a patient with apparatus for monitoring gaseous components of the exhalation of said patient. The system includes a low dead space volume disc filter for blocking patient secretions and natural and manufactured humidification, improved sampling configuration, and apparatus for supporting endotracheal and tracheal tubes and the like with minimum discomfort to the patient. Special provision is made for supporting the endotracheal tube for a neonate, including a wire support requiring only minimal taping.

11 Claims, 8 Drawing Figures

U.S. Patent  Dec. 4, 1984  4,485,822
FIG. 1
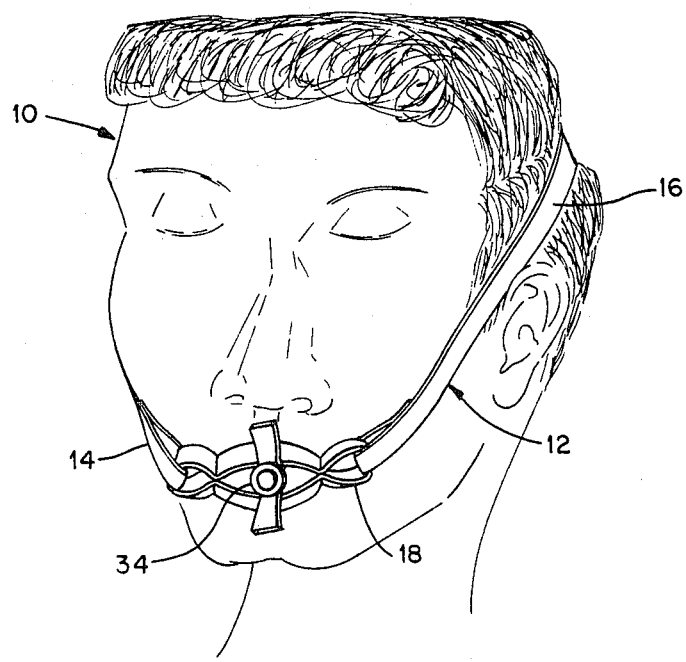
FIG. 2
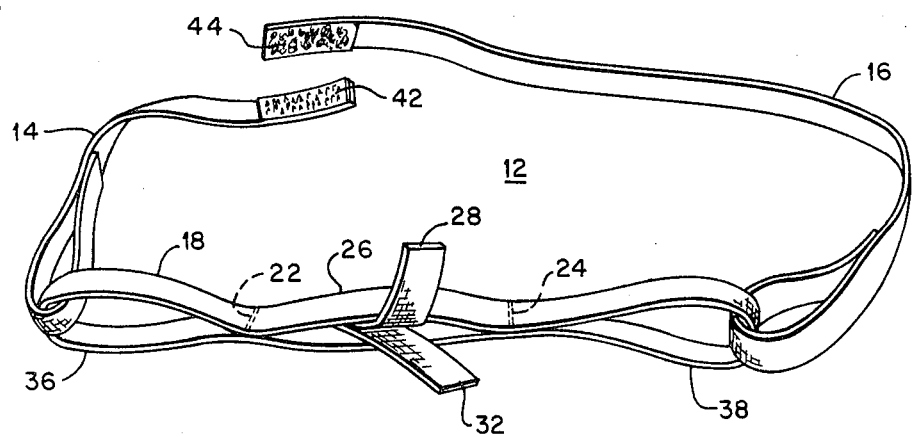
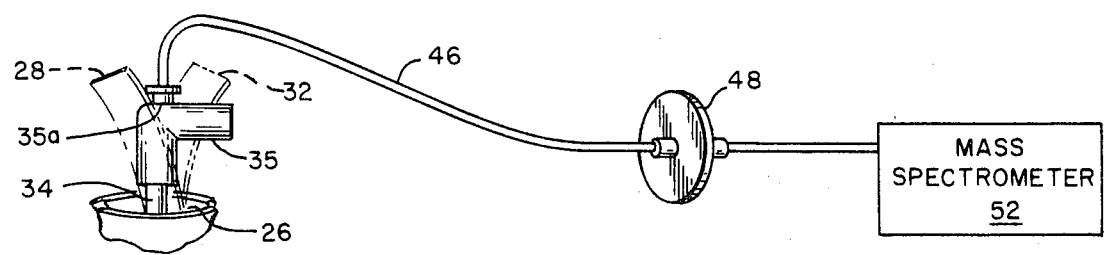
FIG. 3

MULTI-PHASE INTERFACING SYSTEM AND METHOD

BACKGROUND OF THE INVENTION

This invention relates to a system and method for interfacing a patient with equipment for monitoring the expired gas of said patient.

It is often necessary to monitor the condition of hospital patients closely and, typically, patients who require such attention may be found in the intensive care unit, recovery room, coronary care unit, operating room, or in general care areas.

These areas are normally provided with equipment which permits a few hospital personnel to monitor a relatively large number of patients at one time and some of such equipment may involve remotely located displays or measuring devices.

An example of such a system is one which monitors the expired gases of patients for the presence of $CO_2$. A sharp reduction in $CO_2$ for a particular patient could indicate an imminent failure of respiration, and, of course, absence of $CO_2$ would indicate death of the patient. A sharp increase in $CO_2$ could indicate another condition requiring attention.

Measurements of $CO_2$, as well as other gases of interest, can be taken on a continuous basis by the use of a mass spectrometer, and for this purpose provision must be made for delivering continuously a sample of the expired gas to the measuring equipment. Unfortunately, the sampling process usually involves the presence of a certain amount of patient's secretions as well as natural and manufactured humidification which when reaching the mass spectrometer will affect the results. Attempts heretofore to filter out such liquids introduced levels of dead space into the interfacing system which affect adversely the accuracy of results produced by the mass spectrometer.

Another problem generally associated with such interfacing systems and methods has to do with patient comfort. In order to obtain the sample of exhaled breath, an endotracheal tube, nasal cannula, aerosol "T", or even a mask device may be employed, entering the patient either by way of the mouth and/or the nose or surgically through a tracheal incision. In order to hold the tube in place, extensive taping on the face and head of the patient is often required with resulting discomfort as a result of skin tearing and skin sores forming under the tapes. This problem is compounded when the tube has to be removed to permit moving of the patient, or some other procedure is to be performed followed by replacing of the tube and retaping. Also, burn patients can not be taped at all due to existing skin damage.

A variety of attempts have been made to overcome these problems. In U.S. Pat. No. 2,259,817 and 4,018,221 there are shown headbands for use with nasal cannula, but they do not appear to be useful with endotracheal tubes entering through the mouth. Also, it is believed that in these arrangements there is inadequate support where the tubes enter the nostrils. Also, no removal of patient secretions appears to be provided for in these patients.

In U.S. Pat. No. 4,060,074 there is a filter provided but only for removing solid particles from the gases being supplied to the patient. U.S. Pat. No. 4,090,513 shows an arrangement for humidifying the gas being inhaled. Other U.S. Patents of interest are U.S. Pat. Nos. 3,718,135 and 3,910,261, but these do not attempt to deal with the problems described above. Efforts have been made to employ cold traps to remove patient secretions and other liquids, but these have not been successful due to the excessively large dead spaces, in the order of 10–50 cc, which are added to the systems by such traps.

SUMMARY OF THE INVENTION

In this invention the problems mentioned above are largely overcome, and certain other advantages are obtained, by providing an interfacing system and method which provide for exhaled breath sampling during all three stages of patients treatment where monitoring is required. These stages, which may be described as a step down sampling approach, include ventilation followed by humidification, and then sampling alone. The system and method of this invention block the flow of patient secretions and other liquids to the mass spectrometer or other monitoring equipment, reduce dead space to acceptable levels, and at the same time improve patient comfort and simplify the removal and replacement of the endotracheal and other tubes.

By dead space herein is meant any space in the system between the point where the sample is tapped and the point at which the sample enters the mass spectrometer or other measuring device not utilized in the physiological exchange of gases. This would include the space within connecting tubes, filters, valves and traps.

The presence of dead space in the sytem is of course unavoidable, and one effect of the dead space is to introduce a range of possible errors in the results. As the amount of dead space in the system is increased, the margin of possible error, in either direction, also increases. The difference between a reading, for example, of the $CO_2$ level measured by the spectrometer and that determined by chemical blood/gas analysis is referred to as the gradient. One of the purposes of this invention is to reduce gradient levels substantially below values which have been obtainable up to now in present systems and methods of interfacing patients with gas monitors. In this invention, reduced gradient levels are accomplished by reducing dead space in the system while at the same time blocking the flow of patient secretions and other liquids to the monitoring equipment.

In accordance with the principles of this invention there is provided in one preferred embodiment of the invention a tube entering the nasal or oral orifice of a patient to be monitored and terminating with an opening into the nasal pharynx or trachea where the sample is drawn, the tube as it emerges from the orifice being supported without taping on the patient by an elastic headband. A flexible tube may be connected to the tube for delivering the sample to a monitoring device such as a mass spectrometer and a disc filter is located in the flexible tube which blocks liquids and passes only gases. Low dead space throughout the system, especially in the filter, is maintained.

In other embodiments of this invention the sampling system and method described herein may be combined with an inhalation system such as for the delivery of an anesthetic, oxygen, or air, or with a unique supporting arrangement for the endotracheal tube on a neonate.

It is thus a principal object of this invention to provide an improved interfacing system and method for use between a patient and apparatus to monitor the gaseous components of the expired gas of the patient.

Other objects and advantages of this invention will hereinafter become obvious from the following description of preferred embodiments of this invention.

BRIEF DESCRIPTION OF THE DRAWINGS

FIG. 1 is a perspective view of the head of a patient with one preferred embodiment of a headband incorporating the principles of this invention.

FIG. 2 is a perspective view of the headband above.

FIG. 3 shows schematically an interface system embodying the headband shown in FIGS. 1 and 2.

DESCRIPTION OF THE PREFERRED EMBODIMENTS

Figure 4:
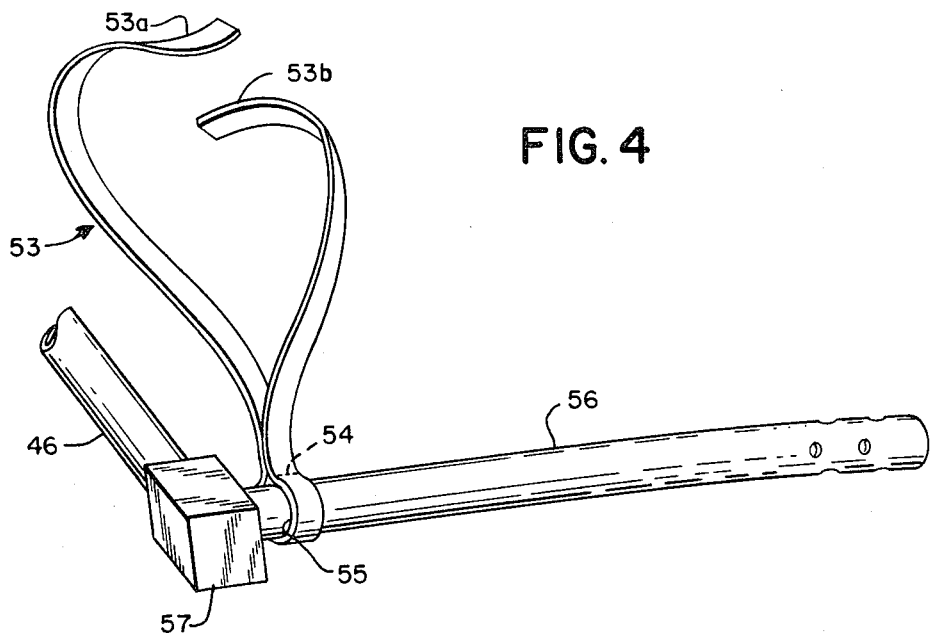
FIG. 4 is an alternative embodiment of the headband shown in FIG. 2.

This invention encompasses a complete system and method for interfacing a patient with apparatus for monitoring and/or supplying breathing assistance. Under some circumstances the system or method would be useful to assist in a variety of other related tasks such as pumping out stomach contents or providing nutrients directly to the stomach.

The invention comprises a variety of embodiments which include not only unique configurations and method steps but components which in themselves represent substantial improvements in the art.

Referring to FIGS. 1, 2, and 3, there is illustrated a system for monitoring $CO_2$ in the expired gas of a patient with a head 10 on which is mounted a headband 12 incorporating certain novel features. Headband 12 consists of a first strap 14, a second strap 16, and a retainer strap 18. All of the straps are constructed of elasticized fabric material and therefore are stretchable.

Retainer strap 18 is a continuous loop stitched together at 22 and 24 forming a central section 26 with a pair of tabs 28 and 32 attached such as by being sewed to the inner surfaces of the two strap portions forming central section 26. Tabs 28 and 32 may also be constructed of elasticized material. By pulling apart tabs 28 and 32 it is possible to open a space through central section 26 to accommodate endotracheal tube 34, shown in FIGS. 1 and 3.

Tube 34 extends into the throat and trachea of patient 10 through his mouth. Tube 34 terminates just out of headband 12 where, as seen in FIG. 3, an elbow 35 may be attached.

In order to hold retainer strap 18 in place, straps 14 and 16 are attached in any convenient fashion to the looped ends 36 and 38, respectively, of strap 18. The free ends of straps 14 and 16 are provided with a friction connection which has become known in the trade as Velcro. This connection consists of a prickly surface 42 on the end of strap 14 and a coarse surface 44 on the end of strap 16. When surfaces 42 and 44 are mated together they are unable to slide apart so that headband 12 stays securely in place, but the strap ends can be readily pulled apart when headband 12 is to be removed. Of course, any other means of attaching the ends of straps 14 and 16, such as a buckle, may be employed.

In the use of headband 12, retainer strap 18 is placed on the mouth of the patient with the edge separating the lips, and straps 14 and 16 are pulled around the head at any convenient location with the ends joined by surfaces 42 and 44. By stretching the straps slightly it is seen that headband 12 will remain securely in place. This configuration allows for suctioning in the oral passages.

Tabs 28 and 32 are then pulled apart to form an opening into which endotracheal tube 34 can be inserted and adjusted so that its end protrudes from headband 12 only enough to accommodate an elbow. As is understood in the art the length of tube 34 is selected so as to terminate within the patient at the desired location.

It should be noted that headband 12 can also be employed to pass around the neck of the patient where a tracheal tube may be inserted through an incision.

As shown in FIG. 3, elbow 35 is press fitted on the exposed end of endotracheal tube 34. One end of a flexible tube or hose 46 is lock-fitted into a sample site opening 35a on elbow 35. The open, unattached end of elbow 35 permits breathing and/or ventilation to take place at the same time that sampling occurs. In tube 46, remote from the patient, is a disc filter 48. The other end of tube 46 terminates in a mass spectrometer 52 which monitors the $CO_2$ present in the expired gas of the patient. As is understood in the art, results as measured by mass spectrometer 52 can be displayed on a CRT, on a printout, or an alarm can be sounded upon some predetermined chance in the values, or any combination of the foregoing. Also, any other gas or gases can be monitored, such as oxygen, nitrogen, carbon monoxide, etc. The various connections, as understood in the art, are Luer slip or lock fittings.

The function of disc filter 48 is to block the secretions of the patient and other liquids as the presence of any liquid in the sample being delivered to spectrometer 52 will interfere with the results. On the other hand the interface system must keep the dead space at the absolute minimum possible so as to have minimum interference with waveform fidelity, resistance to flow, and system vacuum which is maintained in order to keep a constant flow of the sample to spectrometer 52.

For this purpose it has been found that filter 48 should preferably be in the form of a disc with a large surface area as compared to volume, and that pore size must be small enough so as to limit penetration of the non-gaseous component of the sample to only surface penetration. It has been found that a disc filter in this invention should not have openings in excess of 0.5 microns to the sample flow. In addition, the filter should be located as far from the patient, and as close to the monitor as is possible to reduce the presence of liquids at the filter. Under some circumstances it may be desirable to utilize two such filters in which case one filter would be close to the patient and the other filter close to the monitoring apparatus. It should be noted that a disc type filter is capable of providing low dead space as compared to other filter types which lack this capability.

A disc filter unit which has been found suitable for this system is one which is made available commercially by Millipore Corporation of Bedford, Mass. Such a filter unit is identified as a Millex-SR Filter Unit with a 0.5 μm PTFE membrane.

Headband 12 illustrated in FIG. 2 is designed specifically for use with the mouth of tracheostomy of the patient. When it is desired to support a tube entering the patient through his nose, such as a nasal catheter, the headband illustrated in FIG. 4 would be employed.

Referring to FIG. 4, headband 53 consists of a single band of elasticized fabric stitched together at 54 to form a loop 55 through which a nostril catheter 56 is inserted. The free ends 53a and 53b of headband 53 would be wrapped around the head of the patient as described above and would be clamped together using a Velcro connection as described above or any other type of suitable connecting means.

Catheter 56 extends through the nose of the patient and terminates at a point determined by its length. Loop 55 holds an end of catheter 56 just at the entrance to the nostrils and a transition piece 57 is provided to connect the exposed end of catheter 56 to tube 46 making a right angle turn in direction of flow at the nose.

In the use of headband 53, it will be seen that loop 55 will be located just at the entrance to the nostrils of the patient with catheter 56 extending into the nose and tube 46 coming away from the patient at right angles to catheter 56. As in the previously described headband, no taping is required. Also, in the use of headbands 12 (in FIG. 2) and 53 (in FIG. 4), the supports for the sampling tube are out of patient view so that in addition to providing physical comfort to the patient there is a psychological benefit as well.

In the system described above, the gaseous content of the expired gases of a patient is monitored effectively, efficiently, accurately, and with little or no interference due to patient secretions and other liquids present. This is the third stage of patient monitoring, mentioned above, where sampling alone takes place.

Very often, however, this monitoring takes place during the first or second stages, when the patient is receiving respiratory assistance, ventilation, an enriched oxygen breathing mixture, or an anesthetic, or any combination of the foregoing.

Figure 5:
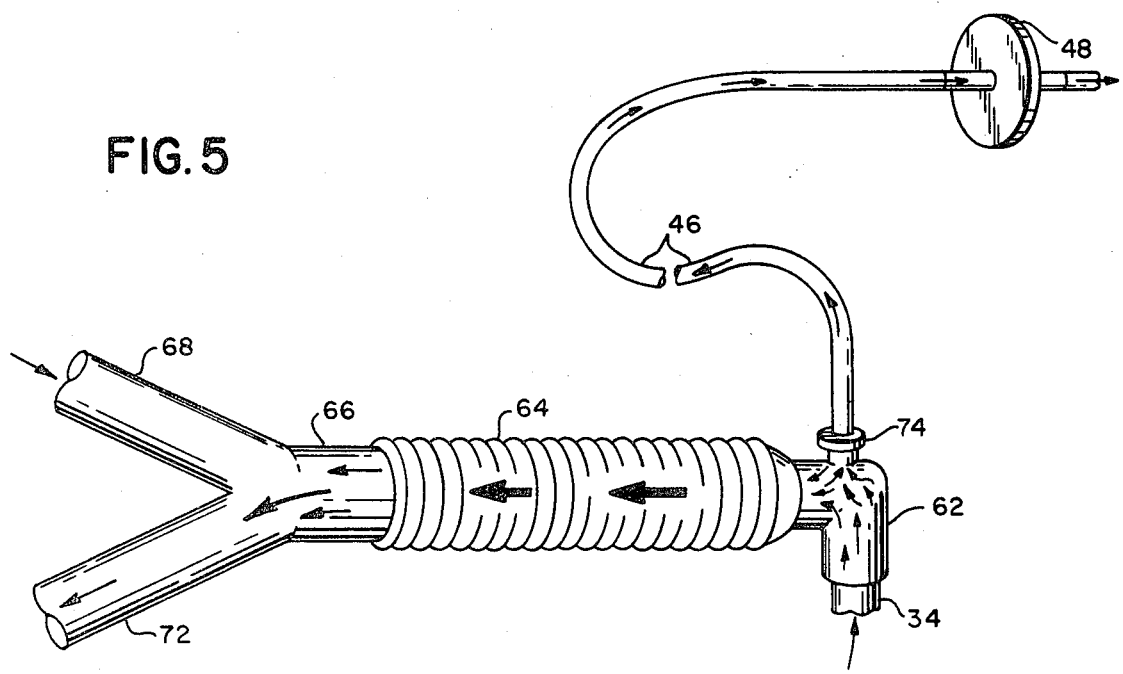
FIG. 5 shows an interface system which provides for simultaneous monitoring of gases and supplying of gases to the patient.

A system which is capable of combining monitoring with any of the other functions is illustrated, somewhat schematically, in FIG. 5. This system consists of an elbow 62 mounted on endotracheal tube 34 and connected at its other end to a flex tube 64 in which respiratory gases from the patient mix with the gases being supplied, and Y-member 66 which has legs 68 and 72 for the inhalation and exhalation gases, respectively. The use of a flex tube and a Y-member to permit the mixing of the gases is known in the art and is in use.

A suction connector 74 on elbow 62 permits the connection of flexible tube 46 to permit the sample under suction to be carried to the monitor through disc filter 48 of the type previously described and to block secretions and other liquids as hereinabove described. In this arrangement, also, disc filter 48 is located away from its elbow 62. The use of headband 23 shown in FIGS. 1 and 2 or headband 53 shown in FIG. 4 permits the patient to be attached to the interface system with little or no discomfort, and it is convenient and easy to disengage the patient and then reconnect him whenever this is required, avoiding completely the use of bandages. Dead space is measured in this configuration from connector 74 at point of sampling.

Under some circumstances it is desirable to attach flexible tube 46 to obtain the sample at a place which is remote from elbow 62. This might be done if it is desirable to reduce the weight and tension applied to the endotracheal tube and to reduce by gravity the sections entering tube 46.

Figure 6:
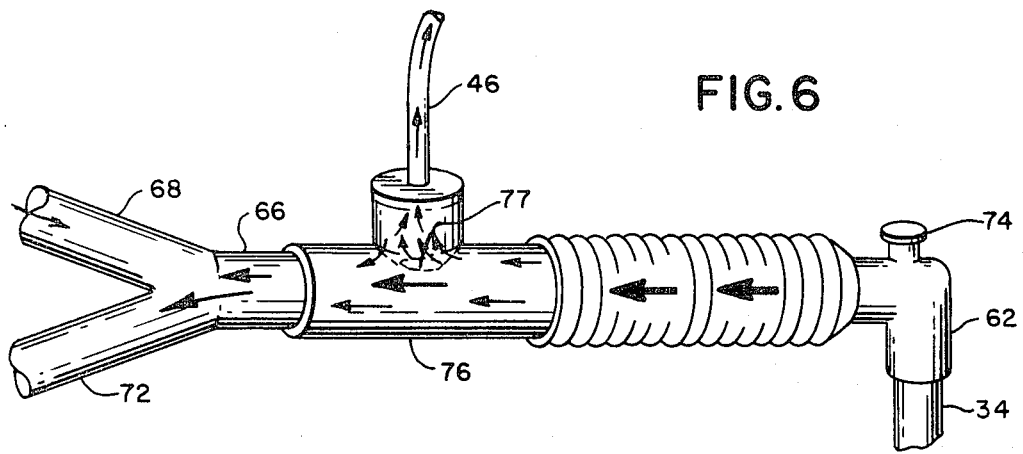
FIG. 6 is an alternative embodiment of the interface system.

Such an arrangement is shown in FIG. 6 where a T-connector 76 is inserted between flex tube 64 and Y-connector 66 and tube 46 is connected through the former. Within T-connector 76 is provided a skirt 77 to block moisture flow into tube 46 should the latter be pointed in a downward direction. Connector 74 is closed. The arrangements shown in FIGS. 5 and 6 relate to the first stage of patient monitoring wherein at the same time that sampling occurs ventilation is also provided.

Figure 7:
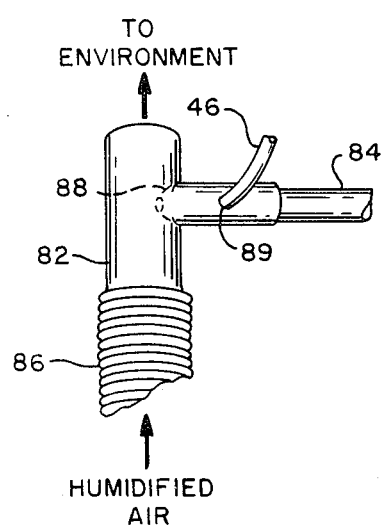
FIG. 7 is another alternative embodiment of the interface system.

A suitable second stage arrangement where only humidification is provided while sampling is conducted is shown in FIG. 7 In this configuration, a T-member 82 is connected to tube 84 which enters the patient either through the nostrils, or mouth, or incision and could be supported by use of the headbands previously described. A flex tube 86 for supplying the humidified air is connected to one end of member 82, and the other end is open to the environment where the humidified air and exhalant are discharged. Member 82 is provided with a skirt 88 as previously described. Sampling tube 46 draws its sample from an opening 89 on the leg of the T-member just where tube 84 is connected.

A special problem exists when the interfacing is used with a neonate, that is, a prematurely born infant, due to the very small size of the face and the soft body structure which mitigates against the use of a headband.

Figure 8:
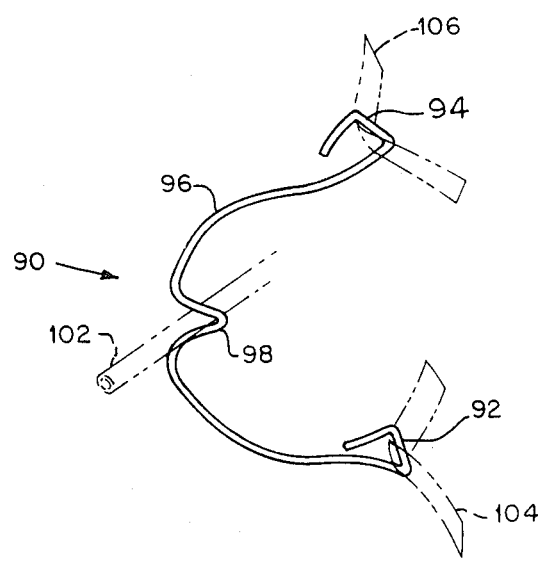
FIG. 8 is a perspective view of a support for an endotracheal tube for use on the face of a neonate.

To hold the end of the endotracheal tube, which can enter either a nostril or the mouth, there is provided according to the principles of this invention a support 90 shown in FIG. 8.

Support 90 may be constructed of a single length of a wire coated with a soft plastic material. The coated wire is bent to form a pair of straight supporting segments on legs 92 and 94 in which there is provided a double bend 98 through which the endotracheal tube 102, shown in phantom, passes. On the end of tube 102 would be attached to the elbow or transition member (not shown) while in the other direction the tube would pass through a nostril or the mouth of the neonate.

The free ends of legs 92 and 94 are turned up to avoid making contact with the patient.

In using support 90, the latter is placed on the face of the neonate with legs 92 and 94 touching the skin while tapes 104 and 106, as shown in phantom, are used to hold the former in place. Tube 102 is then inserted into the mouth or nostril of the patient (support 90 being positioned properly for this purpose), and the exposed end of tube 102 is placed in the trough of double bend 98, and the sides of recess 98 are squeezed gently to hold tube 102 in place. Then the elbow and the rest of the system as described above are connected to tube 102.

It should be noted that the use of support 90 requires a minimum of taping and discomfort to the infant yet is quite capable of holding tube 102 in place. Support 90 can be readily altered in shape to conform to the facial features of the neonate thereby enhancing its usefulness as a device which is least burdensome to the infant patient.

It is seen from the above description of the preferred embodiments of this invention that there has been provided an interfacing system for use with a patient and monitoring devices which is simple to use, effective and efficient, and causes minimum discomfort to the patient. The various configurations and methods as described herein make up a total interfacing system and method which provide monitoring of a patient's exhalation during the three stages of care involved, breathing assistance during ventilation and humidification followed by monitoring alone.

While only certain preferred embodiments of this invention have been described, it is understood that many changes and alterations are possible without departing from the principles of this invention as defined in the appended claims.

What is claimed is:

1. Apparatus for sampling the expired gas of a patient and delivering same secretion and liquid free to monitoring means comprising tube means for entering a facial orifice of said patient and terminating within said patient at a point where a sample of exhaled gases is to be extracted, means for mounting on the head of said patient for holding said tube means in place, and low dead space means for delivering said sample to said monitoring means including flexible tube means connected to said tube means for delivering said sample continuously to said monitoring means and including disc shaped filter means whose pore size is no more than 5 μm in said flexible tube means for blocking all liquids.

2. The apparatus of claim 1 in which said holding means is a headband comprising a band of flat, elasticized material forming an endless loop, said loop being flattened into two layers and the two layers attached to each other to form a central passageway, said band having one side edge adapted to be mounted on the face of said patient for pressing between the lips of said patient, means to pull open adjacent layers of said band to open said central passageway sufficient to accommodate said tube means and means to pull said headband taut on said face to hold said tube means securely in place where it enters said patient.

3. The apparatus of claim 2 in which the last-named means comprises straps connected to opposite ends of said loop adapted to be pulled around the head of said patient and having means to attach said straps securely in place.

4. The apparatus of claim 1 in which said holding means is a headband comprising a band of flat, elasticized material and means forming a loop at an intermediate point on said band, said loop supporting one end of said tube means.

5. The apparatus of claim 1 in which said tube means includes a mixing tube for ventilating said exhaled gases and said flexible tube means extracts the sample from a point adjacent said mixing tube.

6. The apparatus of claim 1 having a T-member for supplying humidified air and said tube means terminates in one side of said T-member and said flexible tube means extracts the sample from the other side of said T-member.

7. A headband for use in supporting a tube entering a patient through the mouth thereof comprising a band of flat, elasticized material forming an endless loop, said loop being flattened into two layers and the two layers of material attached to each other at two locations to form a central and two end passageways, first means attached to the two end passageways to mount said band on the face of said patient with side edges of said band layers forming the central passageway for being pressed between the lips of said patient, said first means including means to pull and hold said loop sufficiently taut to maintain said lips parted, and second means mounted on said band at the central passageway thereof to open the central passageway sufficiently wide to permit insertion of said tube, the latter said means upon being released permitting said band of elasticized material to clamp said tube and holding the latter in place as a result of the tautness of said headband.

8. The headband of claim 7 in which said first means consists of straps looped through said end passageways for being extended around the head of said patient and having means to be clamped together holding said headband to any selected degree of tautness.

9. The headband of claim 8 in which said second means consists of pull members attached to the band material on adjacent layers of said central passageway for permitting the layers to be pulled apart.

10. Apparatus for supporting tube means entering a facial orifice of a neonate, means for supporting the end of said tube means as it exits from said orifice having a pair of legs for resting on the face of said neonate, a loop of wire connecting said legs and adjacent sections of said wire forming a deformable passageway through which said tube means passes, said passageway being deformable to hold said tube means in place, said legs including means for permitting taping to the face of said neonate to hold said supporting means in place.

11. A method of sampling the expired gas of a patient and delivering the sample secretion and liquid free to monitoring apparatus during ventilation, humidification, and sampling only stages of patient monitoring comprising the steps of extracting a sample of exhaled gases from said patient, and transmitting under suction said sample on a continuous basis to monitoring apparatus through an interconnection having a low dead space and containing a disc shaped filter blocking all liquid flow to said monitoring apparatus, said filter having a flat surface exposed to sample flow whose pore size is not in excess of five micrometers.

* * * * *